US009408897B2

(12) United States Patent
Levinson et al.

(10) Patent No.: US 9,408,897 B2
(45) Date of Patent: Aug. 9, 2016

(54) VACCINES FOR SUPPRESSING IGE-MEDIATED ALLERGIC DISEASE AND METHODS FOR USING THE SAME

(71) Applicant: THE TRUSTEES OF THE UNIVERSITY OF PENNSYLVANIA, Philadelphia, PA (US)

(72) Inventors: Arnold I. Levinson, Radnor, PA (US); Sandra Calarota, Philadelphia, PA (US); David B. Weiner, Merion, PA (US); Miguel Otero, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 294 days.

(21) Appl. No.: 14/054,621

(22) Filed: Oct. 15, 2013

(65) Prior Publication Data

US 2014/0127244 A1 May 8, 2014

Related U.S. Application Data

(62) Division of application No. 10/518,701, filed as application No. PCT/US03/19383 on Jun. 20, 2003, now abandoned.

(60) Provisional application No. 60/390,304, filed on Jun. 20, 2002.

(51) Int. Cl.

*A61K 48/00* (2006.01)
*A61K 39/00* (2006.01)
*C07K 16/00* (2006.01)
*A61K 39/08* (2006.01)

(52) U.S. Cl.

CPC ............. *A61K 39/0005* (2013.01); *A61K 39/08* (2013.01); *C07K 16/00* (2013.01); *A61K 39/00* (2013.01); *A61K 2039/505* (2013.01); *A61K 2039/53* (2013.01); *C07K 2317/52* (2013.01); *C07K 2318/10* (2013.01); *C07K 2319/55* (2013.01)

(58) Field of Classification Search

None

See application file for complete search history.

(56) References Cited

U.S. PATENT DOCUMENTS

| | | | | |
|---|---|---|---|---|
| 4,022,878 | A | 5/1977 | Gross | |
| 4,329,281 | A | 5/1982 | Christenson et al. | |
| 4,526,716 | A | 7/1985 | Stevens et al. | |
| 4,769,326 | A | 9/1988 | Rutter | |
| 4,945,050 | A | 7/1990 | Sanford et al. | |
| 5,036,006 | A | 7/1991 | Sanford et al. | |
| 5,037,645 | A | 8/1991 | Strahilevitz et al. | |
| 5,091,313 | A | 2/1992 | Chang | |
| 5,112,606 | A | 5/1992 | Shiosaka et al. | |
| 5,342,924 | A | 8/1994 | Chang et al. | |
| 5,580,859 | A | 12/1996 | Felgner et al. | |
| 5,593,972 | A | 1/1997 | Weiner et al. | |
| 5,629,415 | A | 5/1997 | Hollis et al. | |
| 5,676,494 | A | 10/1997 | Ruch et al. | |
| 5,693,325 | A * | 12/1997 | Kahn | C07K 14/005 424/185.1 |
| 5,703,055 | A | 12/1997 | Felgner et al. | |
| 5,739,118 | A | 4/1998 | Carrano et al. | |
| 5,750,395 | A | 5/1998 | Fikes et al. | |
| 5,817,637 | A | 10/1998 | Weiner et al. | |
| 5,830,876 | A | 11/1998 | Weiner et al. | |
| 5,962,428 | A | 10/1999 | Carrano et al. | |
| 5,981,505 | A | 11/1999 | Weiner et al. | |
| 6,080,725 | A | 6/2000 | Marciani et al. | |
| 6,622,468 | B2 | 9/2003 | Lucand et al. | |
| 7,348,138 | B2 * | 3/2008 | Weiner | A61K 38/162 424/218.1 |
| 2002/0171673 | A1 * | 11/2002 | Brown | G06Q 10/06 715/700 |
| 2002/0172673 | A1 | 11/2002 | Klysner et al. | |

FOREIGN PATENT DOCUMENTS

| | | | |
|---|---|---|---|
| DK | WO 0220038 A2 * | 3/2002 | A61K 39/0008 |
| NL | WO 9749425 A1 * | 12/1997 | A61K 39/385 |
| WO | 9416737 | 8/1994 | |
| WO | 9612740 | 5/1996 | |
| WO | WO 9612740 A1 * | 5/1996 | A61K 39/0008 |
| WO | 9749425 | 12/1997 | |
| WO | 9853843 | 12/1998 | |
| WO | 9967293 | 12/1999 | |
| WO | 0220038 | 3/2002 | |

OTHER PUBLICATIONS

Muller et al., J. Immunol. 1983, 131:877-881.*
Jabara et al., J. Immunol., 1993, 151:4528-4533.*
Chu et al., J. Exp. Med., 1993, 178:1381-1390.*

(Continued)

*Primary Examiner* — Michael Szperka
(74) *Attorney, Agent, or Firm* — Riverside Law LLP

(57) ABSTRACT

Nucleic acid molecules that encode a protein comprising at least one epitope of membrane IgE free of epitopes present on the serum IgE, including proteins that further comprise non-IgE T cell helper epitope are disclosed. Vaccines, vectors and host cells that comprise such nucleic acid molecules are disclosed. Isolated proteins, including haptenized proteins, comprising at least one epitope of membrane IgE free of epitopes present on the serum IgE, including proteins that further comprise non-IgE T cell helper epitope are disclosed. Vaccines that comprise and methods of making such proteins and antibodies that specifically bind to such proteins are disclosed. Vaccines that comprise killed or inactivated cells or particles are disclosed. Methods of treating and preventing IgE mediated allergic disease or condition are disclosed.

22 Claims, 8 Drawing Sheets

(56) References Cited

OTHER PUBLICATIONS

Watson et al., Molecular Biology of the Gene, 4th edition, 1987, Benjamin Cummings Publishing Company, Inc., pp. 860, 866, and 875.*

Janeway et al., Immunobiolgy, 3rd edition, Garland Publications, 1997, pp. 3:26-3:31.*

Yang et al., J Infect Dis. Oct. 1, 2001;184(7):809-16. Epub Aug. 29, 2001.*

Berd et al. "Immunization with haptenized, autologous tumor cells induces inflammation of human melanoma metastases". Cancer Res. May 15, 1991;51(10):2731-2734.

Chu et al. "DNA rearrangement can account for in vitro switching to IgG1". J Exp Med. 1993. 178(4):1381-1390.

Francis et al. "Peptide vaccines based on enhanced immunogenicity of peptide epitopes presented with T-cell determinants or hepatitis B core protein." Methods Enzymol. 1989.178:659-676.

Jabara et al. "Sequential switching from mu to epsilon via gamma 4 in human B cells stimulated with IL-4 and hydrocortisone". J Immunol. 1993. 151(9):4528-4533.

Janeway et al. "Immunobiology: the immune system in health and disease". 3rd Edition, 1997, 3:26-3:31.

MacLean et al. "Immunization of breast cancer patients using a synthetic sialyl-Tn glycoconjugate plus Detox adjuvant". Cancer Immunol Immunother. 1993. 36(4):215-22.

Miller, Stephen D., and Henry N. Claman. "The Induction of Hapten-Specific T Cell Tolerance by Using Hapten-Modified Lymphoid Cells I. Characteristics of Tolerance Induction." The Journal of Immunology 117.5 Part 1 (1976): 1519-1526.

Muller et al. "Isolation of immunoglobulin class switch variants from hybridoma lines secreting anti-idiotope antibodies by sequential sublining". J Immunol. 1983. 131(2):877-881.

Sad et al. "Bypass of carrier-induced epitope-specific suppression using a T-helper epitope". Immunology. Aug. 1992;76(4):599-603.

Walls et al., "Vectors for the expression of PCR-amplified immunoglobulin variable domains with human constant regions.", Nucleic Acids Res., 1993, 21(12):2921-2929.

Watson et al. "Molecular biology of the gene." 4thed., Benjamim Cummings Publishing Company, Inc. 1987. pp. 860, 866, and 875.

Yang et al. "Induction of potent Th1-type immune responses from a novel DNA vaccine for West Nile virus New York isolate (WNV-NY1999)". J Infect Dis. 2001. 184(7):809-816.

International Search Report dated Feb. 25, 2005 for International Application No. PCT/US2003/019383.

* cited by examiner

Construction of membrane-bound IgE
II. Construction of a vector insert for expression of a mIgE fused to TT
A. Human mIgE - Tetanus toxoid fusion protein expression cassette
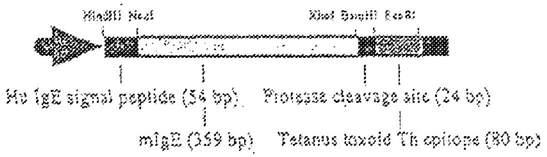
B. PCR amplification with specific primer set
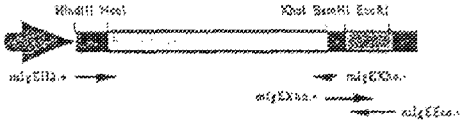
FIG. 2 mIgE-TT construct: Nucleotide and amino acid sequences
(SEQ ID NOS: 5 & 6)

```
atggactggacctggatcctcttcttggtggcagcagccacgcgagtccactcccatggg
 M  D  W  T  W  I  L  F  L  V  A  A  A  T  R  V  H  S | H  G
|_____Leader sequence_____|
```

```
ctggctggcggctccgcgcagtcccagagggccccggatagggtgctctgccactccgga
 L  A  G  G  S  A  Q  S  Q  R  A  P  D  R  V  L  C  H  S  G
|___mIgE_____|
```

```
cagcagcagggactgccgagagcagcaggaggctctgtcccccacccccgctgccactgt
 Q  Q  Q  G  L  P  R  A  A  G  G  S  V  P  H  P  R  C  H  C
|___mIgE_____|
```

```
ggagccgggagggctgactggccaggtcccccagagctggacgtgtgcgtggaggaggcc
 G  A  G  R  A  D  W  P  G  P  P  E  L  D  V  C  V  E  E  A
|___mIgE_____|
```

```
gagggcgaggcgccgtggacgtggaccggcctctgcatcttcgccgcactcttcctgctc
 E  G  E  A  P  W  T  W  T  G  L  C  I  F  A  A  L  F  L  L
|___mIgE_____|
```

```
agcgtgagctacagcgccgccctcacgctcctcatggtgcagcggttcctctcagccacg
 S  V  S  Y  S  A  A  L  T  L  L  M  V  Q  R  F  L  S  A  T
|___mIgE_____|
```

```
cggcaggggaggccccagacctccctcgactacaccaacgtcctccagccccacgccaga
 R  Q  G  R  P  Q  T  S  L  D  Y  T  N  V  L  Q  P  H  A | R
|___mIgE_____|
```

```
gaaaaaagagctgttgttggttacgatccaaattatttaaggactgattctgataaagat
 E  K  R  A  V  V  G  Y  D  P  N  Y  L  R  T  D  S  D  K  D
|__Protease cleavage signal__|          TTp
```

```
agattttacaaaccatggtaaaactgtttaacagaattaagagagaaaaaagagctgtt
 R  F  L  Q  T  M  V  K  L  F  N  R  I  K  R  E  K  R  A  V
 TTp                                       Protease cleavage
```

```
gttggttttaataattttaccgttagcttttggttgagggttcctaaagtatctgctagt
 V  G  F  N  N  F  T  V  S  F  W  L  R  V  P  K  V  S  A  S
 signal              p30TT
```

```
catttagaacatcatcatcatcatcattag
 H  L  E  H  H  H  H  H  H  -
         |____Flag____|
```

Fig.6

Synthetic peptides used as antigens for in vitro assays

| Name | Amino acid sequence | Human migE Region |
|---|---|---|
| IgEEx#1 | (SEQ ID NO: 7) SAQSQRAPDRVLCHSGQQQGLP | extracellular (22 aa) |
| IgEEx#2 | (SEQ ID NO: 8) AGGSVPHPRCHCGAGRADWPGP | extracellular (22 aa) |
| Migis | (SEQ ID NO: 9) ELDVCVEEAEGEAPW | extracellular (15 aa) |
| CTL2 | (SEQ ID NO: 10) EAPWTWTGL | extracellular-transmembrane (9 aa) |
| CTL1 | (SEQ ID NO: 11) TGLCIFAALF | transmembrane (9 aa) |
| IgECyt | (SEQ ID NO: 12) VQRFLSATRQGRPQTSLDYTNVLQPHA | intracellular (27 aa) |
| TTh (27 aa) | (SEQ ID NO: 13) YDPNYLRTDSDKDRFLQTMVKLFNRIK | |

FIG. 7

VACCINES FOR SUPPRESSING IGE-MEDIATED ALLERGIC DISEASE AND METHODS FOR USING THE SAME

FIELD OF THE INVENTION

The present invention relates to vaccines, and to methods for prophylacticallly and/or therapeutically immunizing individuals against IgE mediated allergic.

BACKGROUND OF THE INVENTION

Allergic diseases affect well over 25% of the population in industrialized nations. They account for a substantial amount of morbidity and in some cases, mortality. These diseases include asthma, allergic rhinitis, atopic dermatitis, food allergy, drug allergy, anaphylaxis, and urticaria, amongst others. Despite the development of new pharmaceutical agents like inhaled corticosteroids, non-sedating antihistamines and leukotriene inhibitors, the most prevalent allergic disorders, namely, asthma and allergic rhinitis, continue to represent debilitating and costly conditions, In the U.S. alone, 40 million people suffer from allergic rhinitis at a cost of over $7 billion dollars. Asthma sufferers number over 17 million and account for approximately $10.7 billion dollars in health care-related expenditures.

The lynchpin of allergic inflammation is the IgE immunoglobulin molecule. For some time, it has been appreciated that IgE antibodies specific for environmental allergens bind to specialized receptors on target cells, called mast cells, that are distributed along the tissues that line the respiratory tract, gastrointestinal tract, nerve endings, and blood vessels. The encounter of such IgE-sensitized mast cells with specific allergens, e.g. ragweed pollen, bee venom, or latex protein, triggers the release of many chemical mediators. These, in turn, engender a characteristic pattern of allergic inflammation in the involved tissues and cause allergic symptoms like congested runny nose, itchy eyes, wheezing, shortness of breath, and, in the worst case scenario, cardiovascular collapse and death.

In the past decade, extraordinary gains have been made in our understanding of the cellular and molecular basis of IgE production and regulation of the allergic inflammatory response. It is now appreciated that B cells that give rise to IgE secreting plasma cells do so only with the assistance of so-called helper T cells that also react with the offending allergen. This assistance is provided by a physical interaction of the allergen specific T and B cells and the provision of soluble factors from the T cells to the B cells that foster their maturation into IgE-secreting plasma cells. Such helper T cells are called TH2 cells. By contrast, TH1 cells, another population of helper T cells, inhibit the activity of allergy-promoting TH2 cells by secreting a myriad of counter-regulatory molecules that interfere whit TH2 cell function. It appears that the balance of helper activity in allergic individuals is skewed towards the TH2 cells, thus favoring the development of an IgE/allergic inflammatory response.

Based on this overall mechanistic understanding of the allergic inflammatory response, a number of strategies have emerged to treat allergic diseases like allergic rhinitis and asthma. Several are directed at interdicting the activity of allergen-specific TH2 cells. These include direct inhibition of TH2 cell activity or augmentation of allergen-specific TH1 cell activity with resultant indirect inhibitory action of TH2 cells. Others interfere with IgE-mediated allergic inflammation, e.g., prevention of IgE binding the mast cell receptors and interference with the biochemical signals in allergen-triggered IgE-sensitized mast cells that lead to the release of inflammatory mediators. All of these approaches have shown efficacy in short-term animal models of allergic inflammation including asthma. To date early clinical trials have provided some evidence for clinical efficacy of some of these approaches but their addition to the clinical armamentarium may be limited by toxicity and/or unacceptable expense.

There remains a need for effective compositions and methods for preventing and treating IgE mediated allergic disease and conditions.

SUMMARY OF THE INVENTION

Aspects of the invention relate to nucleic acid molecules that encode a protein comprising at least one epitope of membrane IgE free of epitopes present on the serum IgE, The nucleic acid molecule may further comprise coding sequences encoding a non-IgE helper T cell epitope. The nucleic acid molecules are free of coding sequences encoding epitopes present on the serum IgE. In some embodiments, the nucleic acid molecules that encode protein consisting of the membrane or a fragment thereof. In some embodiments, the nucleic acid molecules that encode isolated protein consists of the membrane. In some embodiments, the nucleic acid molecule is a plasmid.

Aspects of the invention relate to vaccines which comprise such nucleic acid molecules and a pharmaceutically acceptable carrier or diluent. Such vaccines are free of epitopes from serum IgE and free of nucleic acid molecules that contain coding sequences encoding epitopes present on the serum IgE. Such vaccines may comprise coding sequences encoding a non-IgE helper T cell epitope or a peptide that is a non-IgE helper T cell epitope.

Aspects of the invention relate to vectors that comprise nucleic acid molecules that encode a protein comprising at least one epitope of membrane IgE free of epitopes present on the serum IgE. The vector is free of epitopes from serum IgE and free of nucleic acid molecules that contain coding sequences encoding epitopes present on the serum IgE. The vector may further comprise coding sequences encoding a non-IgE helper T cell epitope or a peptide that is a non-IgE helper T cell epitope. In some embodiments, the vector comprises a nucleic acid molecule that encodes a protein that consists of membrane IgE or a fragment thereof. In some embodiments, the vector comprises a nucleic acid molecule that encodes a protein that consists of membrane IgE. In some embodiments, the vector is a virus or a bacterial cell. In some embodiments, the vector is a recombinant vaccinia virus.

Aspects of the invention relate to vaccines which comprise such vectors and a pharmaceutically acceptable carrier or diluent. Such vaccines are free of epitopes from serum IgE and free of nucleic acid molecules that contain coding sequences encoding epitopes present on the serum IgE. The vaccines may further comprise coding sequences encoding a non-IgE helper T cell epitope or a peptide that is a non-IgE helper T cell epitope.

Aspects of the invention relate to an isolated protein comprising at least one epitope of membrane IgE free of epitopes present on the serum IgE. The protein may be a fusion protein which additionally comprises a non-IgE helper T cell epitope. In some embodiments, the isolated protein consists of the membrane IgE or a fragment thereof. In some embodiments, the isolated protein consists of the membrane IgE. In some embodiments, the protein is haptenized.

Aspects of the invention relate to vaccines which comprise such proteins or fusion proteins and a pharmaceutically acceptable carrier or diluent. Such vaccines are free of epitopes from serum IgE and free of nucleic acid molecules that contain coding sequences encoding epitopes present on the serum IgE and may a non-IgE helper T cell epitope wither as part of a fusion protein or as a different peptide or protein.

Aspects of the invention relate to killed or inactivated cells or particles that comprise a protein comprising at least one epitope of membrane IgE free of epitopes present on the serum IgE. The killed or inactivated cell or particles are free of epitopes from serum IgE and free of nucleic acid molecules that contain coding sequences encoding epitopes present on the serum IgE. The killed or inactivated cells or particles may further comprise coding sequences encoding a non-IgE helper T cell epitope or a peptide that is a non-IgE helper T cell epitope. In some embodiments, the killed or inactivated cells or particles comprise membrane IgE protein or a fragment thereof and/or nucleic acid molecules that contain coding sequences encoding membrane IgE protein or a fragment thereof. In some embodiments, the killed or inactivated cells or particles comprise membrane IgE protein and/or nucleic acid molecules that contain coding sequences encoding membrane IgE protein. In some embodiments, the killed or inactivated cells or particles is a killed or inactivated B cell. In some embodiments, the killed or inactivated cells or particles is haptenized.

Aspects of the invention relate to vaccines which comprise such killed or inactivated cells or particles and a pharmaceutically acceptable carrier or diluent. Such vaccines are free of epitopes from serum IgE and free of nucleic acid molecules that contain coding sequences encoding epitopes present on the serum IgE. IgE. The vaccine may further comprise coding sequences encoding a non-IgE helper T cell epitope or a peptide that is a non-IgE helper T cell epitope.

Aspects of the present invention relate to methods of treating an individual suffering from IgE mediated allergic disease or condition. The method comprises administering to such an individual a therapeutically effective amount of a vaccine of the invention.

Aspects of the present invention relate to methods of preventing IgE mediated allergic disease or condition in an individual. The method comprises administering to an individual a therapeutically effective amount of a vaccine of the invention.

BRIEF DESCRIPTION OF THE FIGURES

FIG. 1 shows the cloning of human membrane bound IgE by RT-PCR including a schematic representation of the secretory and two membrane human IgE isoforms and the RT-PCR strategy to amplify membrane bound long form IgE.

FIG. 2 diagrams the construction of a gene construct encoding membrane IgE. FIG. 2 shows the construction of the vector insert for expression of a membrane IgE fused to tetanus toxoid including a schematic representation of the a membrane IgE-tetanus toxoid fusion protein expression cassette and PCR amplification with specific primer set.

FIG. 6 shows the nucleotide and amino acid sequences of an membrane IgE tetanus toxoid construct.

FIG. 7 is a table of synthetic peptides used as antigens in in vitro assays.

DETAILED DESCRIPTION OF PREFERRED EMBODIMENTS

Figure 1:
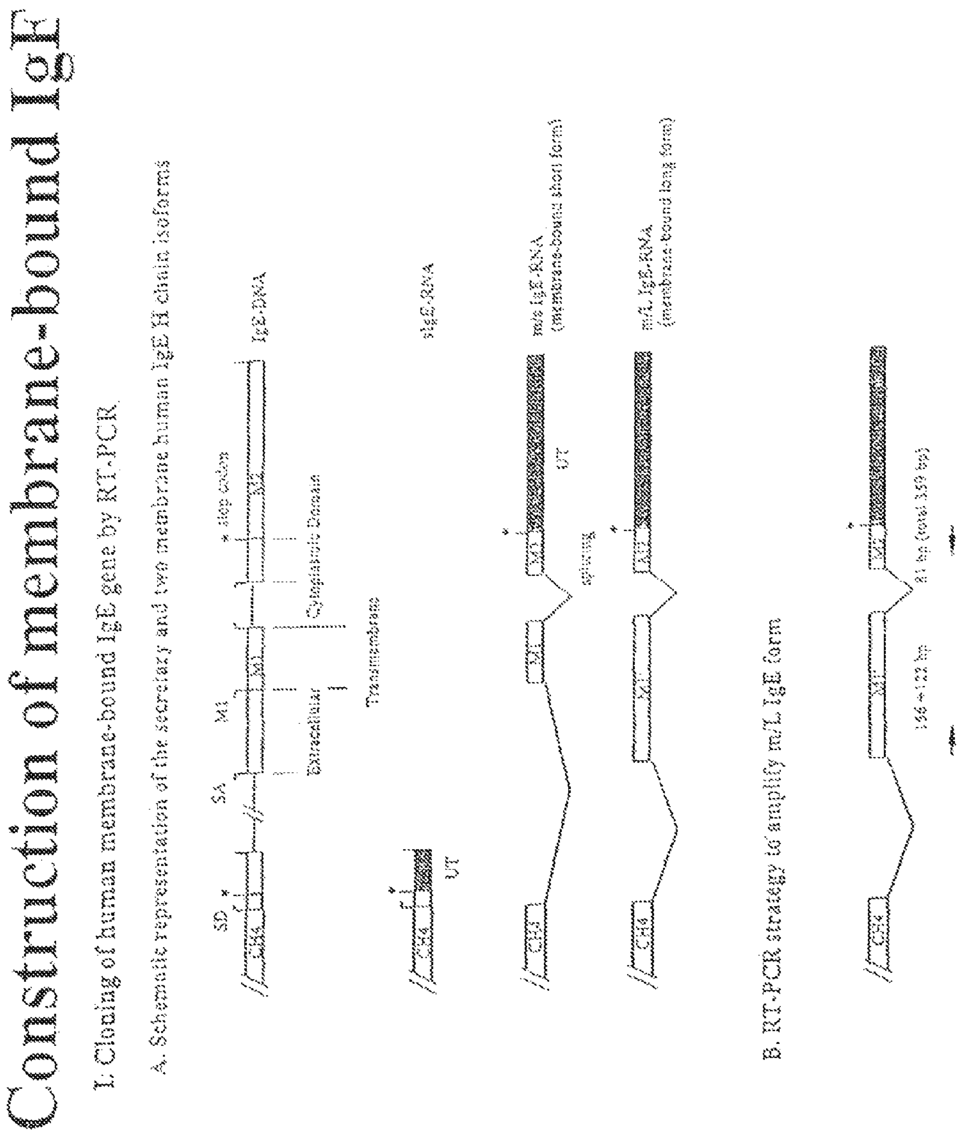
FIG. 1 diagrams the construction of a gene construct encoding membrane IgE.

As used herein, the terms "membrane IgE" and mIgE are used interchangeably and meant to refer, unless further more specifically identified as being the short or long form, either of the two membrane bound forms of IgE (the membrane bound short form m/sIgE and the membrane bound long form m/IgE) as distinguished from the secreted isoform, serum IgE (sIgE). FIG. 1 includes schematic diagrams showing the three isoforms.

As used herein, the term "target protein" is meant to refer to a protein which comprises at least one epitope of membrane IgE and is free of any serum IgE epitopes. In some embodiments, the target protein is a membrane IgE or fragment thereof. In some embodiments, the target protein is the long form of the membrane IgE or fragment thereof. In some embodiments, the target protein is the short form of membrane IgE or fragment thereof. The target protein preferably includes a non-IgE helper T cell epitope. The preferred non-IgE helper T cell epitope is a helper T cell epitope from tetanus toxoid. In some embodiments, the target protein is a fusion protein comprising at least one epitope of membrane IgE and a non-IgE helper T cell epitope, free of any serum IgE epitopes wherein the between one or more epitopes of membrane IgE and the non-IgE helper T cell epitope is a proteolytic cleavage site.

As used herein, the term "genetic construct" refers to the DNA or RNA molecules that comprise a nucleotide sequence, which encodes a target protein or immunomodulating protein. The coding sequence includes initiation and termination signals operably linked to regulatory elements including a promoter and polyadenylation signal capable of directing expression in the cells of the individual to whom the nucleic acid molecule is administered.

As used herein, the term "expressible form" refers to gene constructs which contain the necessary regulatory elements operable linked to a coding sequence that encodes a target protein or an immunomodulating protein, such that when present in the cell of the individual, the coding sequence will be expressed.

The present invention provides vaccines and methods for prophylactically and/or therapeutically immunizing individuals against IgE mediated allergic by targeting IgE-expressing B cells. By immunizing the allergic patient to components of IgE that are exclusively expressed on the B cell membrane (membrane IgE), this population of B cells is eradicated or at least substantially reduce in number, thus removing the source of IgE production.

B cell membrane IgE structure differs from that of IgE in the serum (which finds its way to the surface of mast cells) by containing an additional protein fragment that is found in its cytoplasmic, transmembrane, and membrane-proximal extracellular domains. Accordingly, it should be possible to generate an immune response against components of membrane IgE that will not react with serum IgE. Such an immune response will not be competed by in the serum and will not target IgE sitting on mast cells. Therefore, patients will not be at risk for potentially deleterious mast cell release reactions. Importantly, these membrane IgE components differ significantly from the B cell membrane constituents of IgG and IgM. Therefore, B cells expressing these immunoglobulin isotypes, which represent critical players in normal host defense, will not be targeted.

According to the invention, immune responses to IgE bearing B cells are elicited. These immune responses make it possible for the allergic host to scuttle not only IgE bearing B cells in the extant immune repertoire but also those that might develop in the future. This approach has important advantages over a monoclonal anti-IgE antibody, which targets serum IgE. The latter biologic agent requires multiple injections of extremely costly compositions, and its use will likely be limited to a small subset of allergic individuals. By contrast, the immunotherapeutic strategy employed in the present invention requires limited patient encounters and will be very inexpensive to mass-produce. Accordingly, it should enjoy widespread use amongst populations of allergic patients.

According to some embodiments of the invention, the target protein is delivered to an individual to elicit an immune response against the B cells include delivering the target protein using nucleic acid molecules that encode the target protein. When the nucleic acid molecules that encode the target protein are taken up by cells of the individual the nucleotide sequences that encode the target protein is expressed in the cells and the proteins are thereby delivered to the individual. Aspects of the invention include methods of delivering the coding sequences of the target protein on an isolated nucleic acid molecule, such as a plasmid or as part of recombinant vaccines.

According to some embodiments of the invention, the target protein is delivered to an individual to elicit an immune response against the B cells that include the target protein by delivering the target protein as a protein. Aspects of the invention include methods of delivering the target protein as a protein/peptide, as a haptenized protein/peptide, as a cell or particle that comprises the protein/peptide, or as a haptenized cell or particle that comprises the protein/peptide.

According to some aspects of the present invention, compositions and methods are provided which prophylactically and/or therapeutically immunize an individual against a pathogen or abnormal, disease-related cells. The vaccine may be any type of vaccine such as, a subunit vaccine, a cell vaccine, a recombinant vaccine or a nucleic, acid or DNA vaccine. By delivering the target protein or nucleic acid molecules that encode the target protein, the immune response induced by the vaccine may be modulated.

Regardless of the modality, compositions useful in the invention generally comprise a non IgE helper T cell epitope for provide T cell to induce an effective immune response, either as part of the target protein and/or as a separate protein. If the non IgE helper T cell epitope is part of a fusion protein that is the target protein, the fusion protein may preferably contain proteolytic cleavage sites between the membrane IgE epitope and the non IgE helper T cell epitope. The non-IgE helper T cell epitope is preferably tetanus toxoid helper T cell epitope. If the vaccine is provided and a nucleic acid molecule, a nucleotide sequence is provided that encodes a non IgE helper T cell epitope, preferably tetanus toxoid helper T cell epitope. Thus, some aspects of the invention comprise nucleic acid molecule that encode the target protein and a non IgE helper T cell epitope. Some aspects of the invention relate to composition comprising two nucleic acid molecules, one that encodes the target protein and one that encodes a non IgE helper T cell epitope. If the vaccine is provided and a protein based vaccine, a protein is provided that comprises a non IgE helper T cell epitope, preferably tetanus toxoid helper T cell epitope. Thus, some aspects of the invention comprise the target proteins that comprise a non IgE helper T cell epitope. Some aspects of the invention relate to composition comprising two protein molecules, the target protein and a non IgE helper T cell epitope.

According to the present invention, the membrane IgE serves as a target against which a protective and therapeutic immune response can be induced. Specifically, vaccines are provided which induce an immune response against the membrane IgE. The vaccines of the invention include, but are not limited to, the following vaccine technologies:

1) DNA vaccines, i.e. vaccines in which DNA that encodes at least an epitope from membrane IgE is administered to an individual's cells where the epitope is expressed and serves as a target for an immune response;

2) infectious vector mediated vaccines such as recombinant adenovirus, vaccinia, *Salmonella*, and BCG wherein the vector carries genetic information that encodes at least an epitope of membrane IgE such that when the infectious vector is administered to an individual, the epitope is expressed and serves as a target for an immune response;

3) killed or inactivated vaccines which a) comprise either killed cells or inactivated viral particles that display at least an epitope of the membrane IgE and b) when administered to an individual serves as a target for an immune response;

3) haptenized killed or inactivated vaccines which a) comprise either killed cells or inactivated viral particles that display at least an epitope of membrane IgE, b) are haptenized to be more immunogenic and c) when administered to an individual serves as a target for an immune response;

4) subunit vaccines which are vaccines that include protein molecules that include at least an epitope membrane IgE; and 5) haptenized subunit vaccines which are vaccines that a) include protein molecules that include at least an epitope membrane IgE and b) are haptenized to be more immunogenic.

The present invention relates to administering to an individual a protein or nucleic acid molecule that comprises or encodes, respectively, the target protein, which includes at least one epitope from the membrane IgE, against which an therapeutic and prophylactic immune response can be induced. Epitopes are generally at least 6-8 amino acids in length. The vaccines of the invention therefore comprise proteins which are at least, or nucleic acids which encode at least 6-8 amino acids in length from membrane IgE. In some embodiments the target protein contains at least 6 mIgE amino acid sequences. In some embodiments the target protein contains at least 10 mIgE amino acid sequences. In some embodiments the target protein contains at least 15 mIgE amino acid sequences. In some embodiments the target protein contains at least 20 mIgE amino acid sequences. In some embodiments the target protein contains at least 25 mIgE amino acid sequences. In some embodiments the target protein contains at least 30 mIgE amino acid sequences. In some embodiments the target protein contains at least 35 mIgE amino acid sequences. In some embodiments the target protein contains at least 40 mIgE amino acid sequences. In some embodiments the target protein contains at least 45 mIgE amino acid sequences. In some embodiments the target protein contains at least 50 mIgE amino acid sequences. In some embodiments the target protein contains at least 55 mIgE amino acid sequences. In some embodiments the target protein contains at least 60 mIgE amino acid sequences. In some embodiments the target protein contains at least 65 mIgE amino acid sequences. In some embodiments the target protein contains at least 70 mIgE amino acid sequences. In some embodiments the target protein contains at least 75 mIgE amino acid sequences. In some embodiments the target protein contains full length mIgE amino acid sequences. It is intended that fragment of mIgE can be used as the part of or as the target protein which comprise any size fragment of the group of fragments from more than 6 up to full length which include at least one epitope. With the required T cell help induced by a non-IgE epitope, such fragments will induce immune response to eliminate B cells. Immune response include CTL responses and/or antibody production. In some embodiments, the antibodies so produced may be isolated.

Nucleic acid molecules encoding a target protein comprising a membrane IgE epitope may be delivered using any of several well known technologies including DNA injection (also referred to as DNA vaccination), recombinant vectors such as recombinant adenovims, recombinant adenovirus associated virus and recombinant vaccinia.

DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference.

Routes of administration include, but are not limited to, intramuscular, intransally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include to mucosal tissue, intramuscular, intraperitoneal, intradermal and subcutaneous injection. Genetic constructs may be administered by means including, but not limited to, traditional syringes, needleless injection devices, or "microprojectile bombardment gone guns".

When taken up by a cell, the genetic construct(s) may remain present in the cell as a. functioning extracbromosomal molecule and/or integrate into the cell's chromosomal DNA. DNA may be introduced into cells where it remains as separate genetic material in the form of a plasmid or plasmids. Alternatively, linear DNA that can integrate into the chromosome may be introduced into the cell. When introducing DNA into the cell, reagents that promote DNA integration into chromosomes may be added. DNA sequences that are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors that live in cells. Gene constructs may be part of genomes of recombinant viral vaccines where the genetic material either integrates into the chromosome of the cell or remains extrachromosomal. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (MV) such as the BIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal, which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration. Plasmids pVAX is a useful vector.

In some preferred embodiments, the IgE signal peptide is included as part of the target protein.

In some preferred embodiments related to immunization applications, nucleic acid molecule(s) are delivered which include nucleotide sequences that encode a target protein, the immunomodulating protein and, additionally, genes for proteins which further enhance the immune response against such target proteins. Examples of such genes are those which encode other cytokines and lymphokines such as alpha-interferon, gamma-interferon, platelet derived growth factor (PDGF), TNF, GM-CSF, epidermal growth factor (EGF), IL-1, IL-2, Il-4, IL-6, IL-10, IL-12 and IL-15 including IL-15 having the signal sequence deleted and optionally including the signal peptide from IgE.

An additional element may be added which serves as a target for cell destruction if it is desirable to eliminate cells receiving the genetic construct for any reason. A herpes thymidine kinase (tk) gene in an expressible form can be included in the genetic construct. The drug gangcyclovir can be administered to the individual and that drug will cause the selective killing of any cell producing tk, thus, providing the means for the selective destruction of cells with the genetic construct.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs that are functional in the cells.

One method of the present invention comprises the steps of administering nucleic acid molecules intramuscularly, intranasally, intraperatoneally, subcutaneously, intradermally, or topically or by lavage to mucosal tissue selected from the group consisting of inhalation, vaginal, rectal, urethral, buccal and sublingual.

In some embodiments, the nucleic acid molecule is delivered to the cells in conjunction with administration of a polynucleotide function enhancer or a genetic vaccine facilitator agent. Polynucleotide function enhancers are described in U.S. Ser. No. 08/008,342 filed Jan. 26, 1993, U.S. Ser. No. 08/029,336 filed Mar. 11, 1993, U.S. Ser. No. 08/125,012 filed Sep. 21, 1993, and International Application Serial Number PCT/IJS94/00899 filed Jan. 26, 1994, which are each incorporated herein by reference. Genetic vaccine facilitator agents are described in U.S. Ser. No. 0021,579 filed Apr. 1, 1994, which is incorporated herein by reference. The co-agents winch are administered in conjunction with nucleic acid molecules may be administered as a mixture with the nucleic acid molecule or administered separately simultaneously, before or after administration of nucleic acid molecules. In addition, other agents which may function transfecting agents and/or replicating agents and/or inflammatory agents and which may be co-administered with a GVF include growth factors, cytokines and lymphokines such as α-interferon, gamma-interferon, GM-CSF, platelet derived growth factor (PDGF), TNF, epidermal growth factor (EGF), ILA, IL-2, IL-4, IL-6, IL-10, IL-12 and IL-15 as well as fibroblast growth factor, surface active agents such as immune-stimulating complexes (ISCOMS), Freunds incomplete adjuvant, LPS analog including monophosphoryl Lipid A (WL), muramyl peptides, quinone analogs and vesicles such as squalene and squalene, and hyaluronic acid may also be used administered in conjunction with the genetic construct In some embodiments, an immunomodulating protein may be used as a GVF.

The pharmaceutical compositions according to the present-invention comprise about 1 nanogram to about 2000 micrograms of DNA. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

The pharmaceutical compositions according to the present invention are formulated according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

According to some aspects of the present invention, DNA or RNA that encodes a target protein is introduced into the cells of tissue of an individual where it is expressed, thus producing the encoded proteins. The DNA or RNA sequences encoding the target protein and one or both immunomodulating proteins are linked to regulatory elements necessary for expression in the cells of the individual. Regulatory elements for DNA expression include a promoter and a polyadenylation signal. In addition, other elements, such as a Kozak region, may also be included in the genetic construct.

The nucleic acid molecule(s) may be provided as plasmid DNA, the nucleic acid molecules of recombinant vectors or as part of the genetic material provided in an attenuated vaccine or inactivated or killed particle or cell vaccine.

The manufacture and use of subunit vaccines are well known. One having ordinary skill in the art can isolate the nucleic acid molecule that encode target protein. Once isolated, the nucleic acid molecule can be inserted it into an expression vector using standard techniques and readily available starting materials.

In addition to producing these proteins by recombinant techniques, automated peptide synthesizers may also be employed to produce the target protein of the invention. Such techniques are well known to those having ordinary skill in the art and are useful if derivatives which have substitutions not provided for in DNA-encoded protein production.

In some embodiments, the protein that makes up a subunit vaccine or the cells or particles of a killed or inactivated vaccine may be haptenized to increase immunogenicity. In some cases, the haptenization is the conjugation of a larger molecular structure to the target protein. In some cases, cells from the patient are killed and haptenized as a means to make an effective vaccine product. In cases in which other cells, such as bacteria or eukaryotic cells which are provided with the genetic information to make and display the target protein are killed and used as the active vaccine component, such cells are haptenized to increase immunogenicity. Haptenization is well known and can be readily performed.

Methods of haptenizing cells are described in Berd et al. May 1991 *Cancer Research* 51:2731-2734, which are incorporated herein by reference. Additional haptenization protocols are disclosed in Miller et al. 1976 *J. Immunol.* 117(5:1): 1591-1526.

Haptenization compositions and methods which may be adapted to be used to prepare haptenized target protein according to the present invention include those described in the following U.S. Patents which are each incorporated herein by reference: U.S. Pat. No. 5,037,645 issued Aug. 6, 1991 to Strahilevitz; U.S. Pat. No. 5,112,606 issued May 12, 1992 to Shiosaka et al.; U.S. Pat. No. 4,526,716 issued Jul. 2, 1985 to Stevens; U.S. Pat. No. 4,329,281 issued May 11, 1982 to Christenson et al.; and U.S. Pat. No. 4,022,878 issued May 10, 1977 to Gross. Peptide vaccines and methods of enhancing immunogenicity of peptides which may be adapted to modify ST immunogens of the invention are also described in Francis et al. 1989 *Methods of Enzymol.* 178:659-676, which is incorporated herein by reference. Sad et al. 1992 *Immunolology* 76:599-603, which is incorporated herein by reference, teaches methods of making immunotherapeutic vaccines by conjugating gonadotropin releasing hormone to diphtheria toxoid. Target protein may be similarly conjugated to produce an immunotherapeutic vaccine of the present invention. MacLean et al. 1993 *Cancer Immunol. Immunother.* 36:215-222, which is incorporated herein by reference, describes conjugation methodologies for producing immunotherapeutic vaccines which may be adaptable to produce an immunotherapeutic vaccine of the present invention. The hapten is keyhole limpet hemocyanin which may be conjugated to target protein.

Vaccines according to some aspects of the invention comprise a pharmaceutically acceptable carrier in combination with target protein. Pharmaceutical formulations are well known and pharmaceutical compositions comprising such proteins may be routinely formulated by one having ordinary skill in the art. Suitable pharmaceutical carriers are described in *Remington's Pharmaceutical Sciences*, A. Osol, a standard reference text in this field, which is incorporated herein by reference. The present invention relates to an injectable pharmaceutical composition that comprises a pharmaceutically acceptable carrier and a target protein. target protein is preferably sterile and combined with a sterile pharmaceutical carrier.

In some embodiments, for example, the target protein can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise the target protein in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

The vaccines of the present invention may be administered by any means that enables the target protein to be presented to the body's immune system for recognition and induction of an immunogenic response. Pharmaceutical compositions may be administered parenterally, i.e., intravenous, subcutaneous, intramuscular.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. An amount of immunogen is delivered to induce a protective or therapeutically effective immune response. Those having ordinary skill in the art can readily determine the range and optimal dosage by route methods.

Target proteins including target proteins that are fusion proteins can be produced by recombinant technology wherein nucleic acid molecules that encode the target protein are constructed and inserted into expression vectors such as plasmids or viral vectors. The expression vectors contain regulatory elements that function in host cells. When the expression vectors are incorporated into host cells, the target protein is expressed by the host cell. The protein may be isolated using standard techniques including, for example, immunocolumns that include antibodies that specifically bind to the target protein. Antibodies that specifically bind to the target protein can be generated using standard techniques including production of monoclonal antibodies by hybridoma technology.

In addition to uses in protein purification, such antibodies, including Mabs, humanized Mabs, human antibodies, and Fab and F(ab)2 fragments thereof may be used in passive immunity therapy as therapeutic compounds to be administered to patients as an alternative to or in conjunction with the vaccines described herein. Such compositions may be routinely formulated and administered by those skilled in the art following the teachings generally disclosed herein.

Example 1

Strategy for Development of DNA Vaccine for Allergy

There are two forms of IgE, one is secreted (sIgE) and the other is membrane-bound (mIgE) forms (FIG. 1). The mIgE form has two isoforms, short (m/s IgE) and long (m/l Ige) forms. The m/l IgE form was cloned by RT-PCR amplification method. Here after, m/l IgE form will be designated as "mIgE".

Total RNA was extracted from a human myeloid cell line SKO-007 (ATCC #CRL-8033-1) that secretes IgE and is HLA A2 positive. The first cDNA was generated by reverse transcription using oligo-dT, random hexamer, or specific primers for mIgE gene. The mIgE fragment was generated by PCR amplification using specific primer set mIgEH3.S1 (5'-CCC AAGCTT ATG GAC TGG ACC TGG ATC CTC TTC TTG GTG GCA GCA GCC ACG CGA GTC CAC TCC CAT GGG CTG GCT GGC GGC TCC GCG C; SEQ ID NO:1) and mIgEXho.AS1 (5' CCG CTCGAG CGT GGG GCT GGA GGA CGT TGG; SEQ ID NO:2) (FIG. 2). To enhance protein expression level, huIgE leader sequence was fused to 5' end of mIgE fragment (FIG. 2). Moreover, to enhance immune response in vivo, tetanus toxoid Th epitope (TTTh) was fused to mIgE by proteolytic cleavage site. The sequence for proteolytic cleavage site followed by tetanus toxoid Th epitope was generated by overlapping PCR using synthetic oligos, mIgEXho.S1 (5'-CCG CTCGAG AGA AAC GAG CTG TCG TAG GAT CCG ATC CAA ATT ATT TAA GGA CTG ATT CTG ATA AAG ATA GAT TTT TAC AAA CCA TGG; SEQ ID NO:3), mIgEEco.AS1 (5'-CCG GAATTC TTA ATT CTG TTA AAC AGT TTT ACC ATG GTT TGT AAA AAT CTA TCT TTA TCA GAA TCA GTC CTT AAA TAA TTT GGA TCG G; SEQ ID NO:4). The complete human mIgE fused to TTh was constructed by overlapping PCR of mIgE and TTTh fragments, and then cloned into pcDNA3.1V5/His plasmid. The final construct was named as "pcHu-mIgE".

Example 2

In Vitro Protein Expression

1. In Vitro Transcription/Translation and Immunoprecipitation/Western Blot Analysis.

Figure 3:
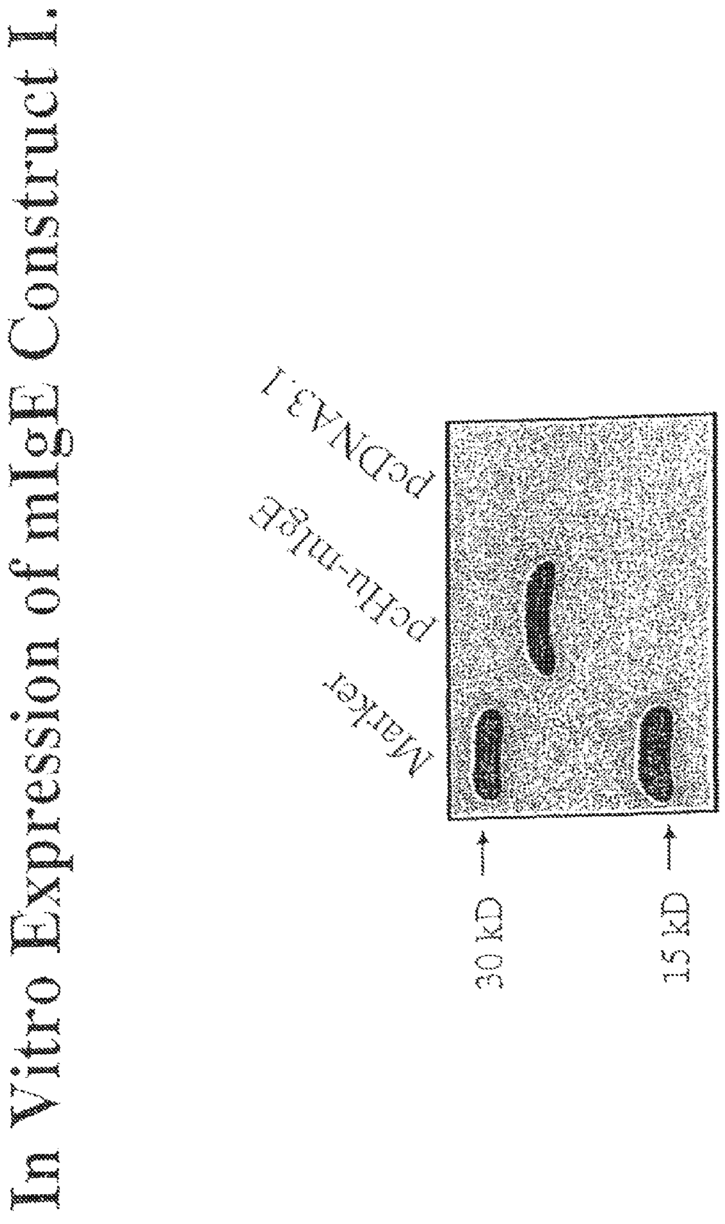
FIG. 3 shows in vitro expression data of a membrane IgE construct.

Two μg of plasmid DNA was transcribed/translated in a single tube using TNT-T7 coupled Transcription/Translation System (Promega) according to the Manufacturer's protocol. The reaction was immunoprecipitated with monoclonal anti-6×His (C-term) Ab along with Protein G-Sepharose beads for overnight. The protein was resolved on 15% of SDS-PAGE and Western blot analyzed with polyclonal anti-6×His Ab. The blot was developed with an ECL Chemiluminescent detection Kit (Amersham). The synthesized protein size was about 20 kD which is close to the predicted protein size (FIG. 3).

2. Protein Expression in Mammalian Cells by Transfection.

Figure 4:
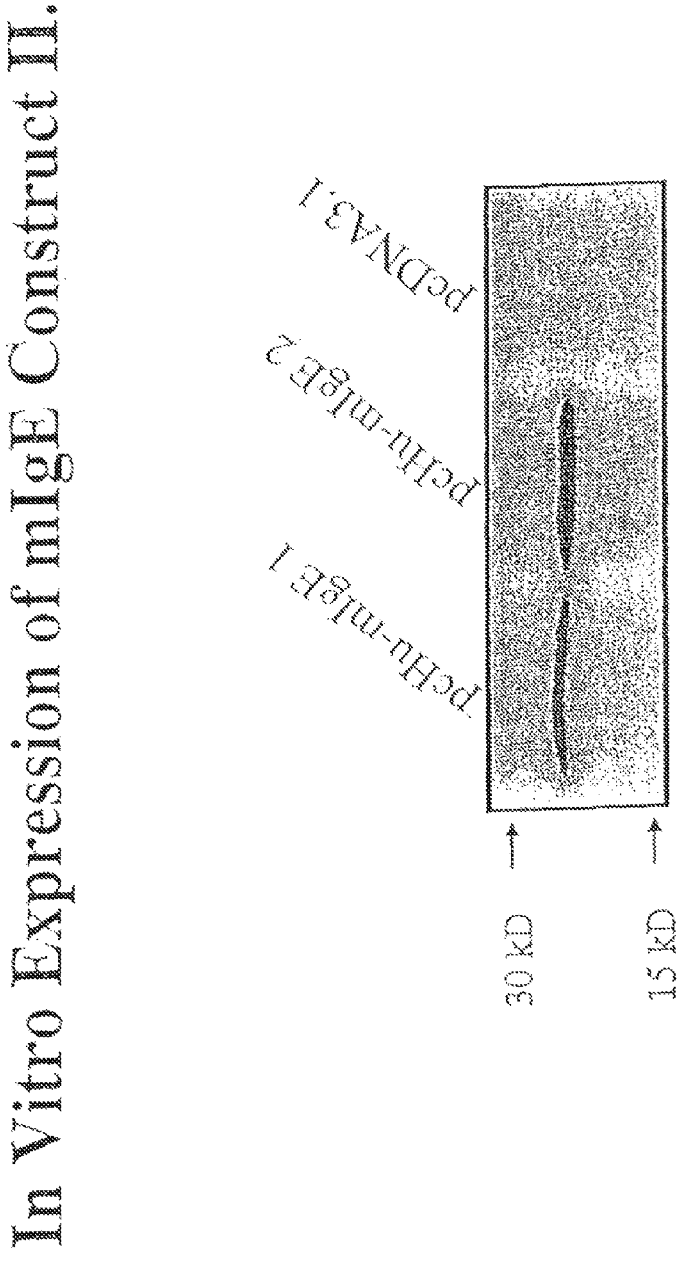
FIG. 4 shows in vitro expression data of membrane IgE constructs.

Two μg of plasmid DNA was transfected to RD cells using DATAP transfection reagent according to the manufacturer's suggestion (Roche). Five days after transfection, cellular proteins were harvested by freezing/thaw method. Hundred μg of total cellular protein was resolved on 15% of SDS-PAGE and Western blot analyzed using polyclonal anti-6×His (C-term) Ab. The blot was developed with an ECL Chemiluminescent detection Kit (Amersham). The synthesized protein size was about 20 kD which is comparable to the size of the in vitro translated protein (FIG. 4).

Example 3

Functional Analysis of a Vaccine for IgE Producing B Cells

Figure 5:
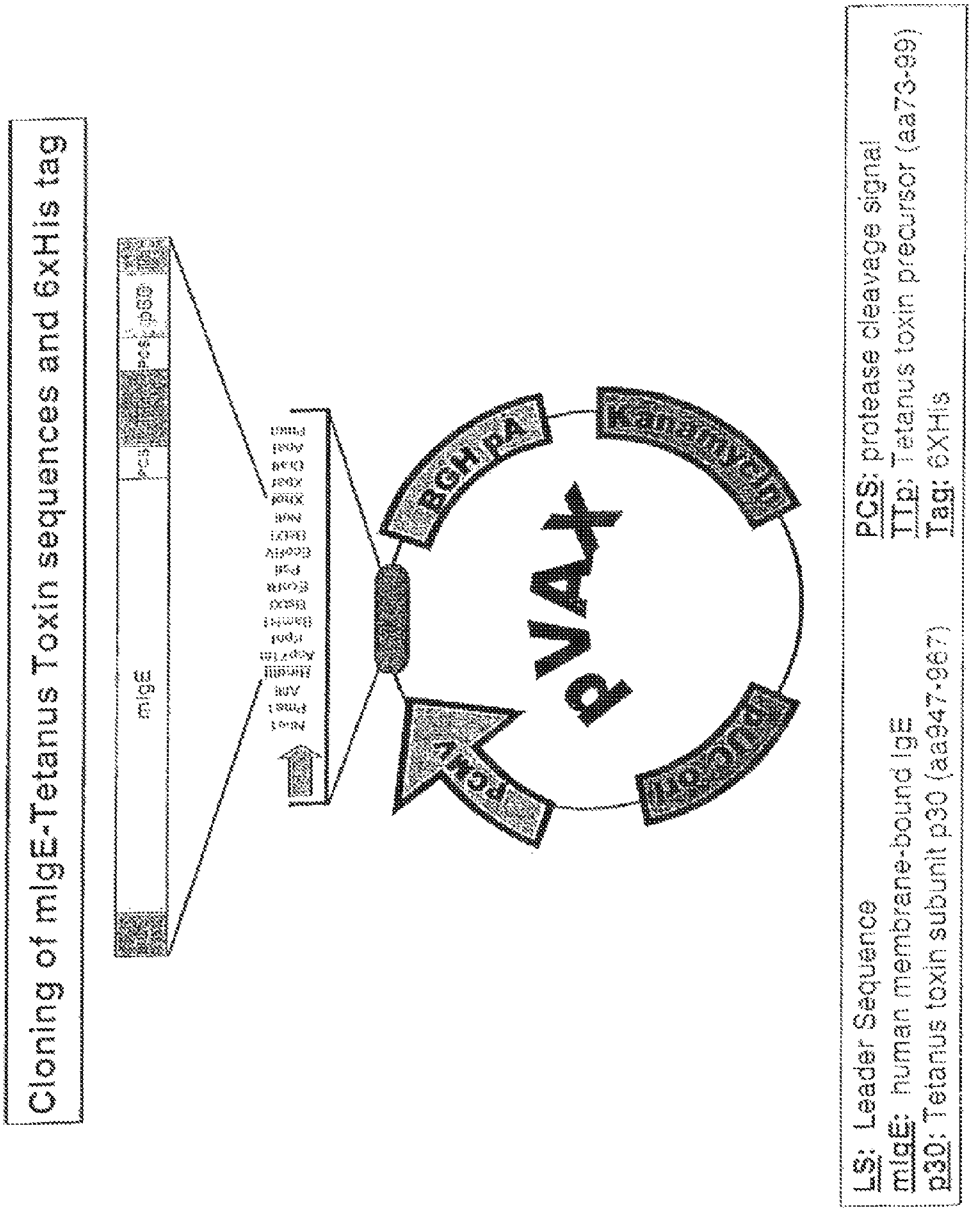
FIG. 5 shows a diagram of the cloning of membrane IgE tetanus toxoid sequences and 6×HisTag into the pVAX vector.
Figure 8:
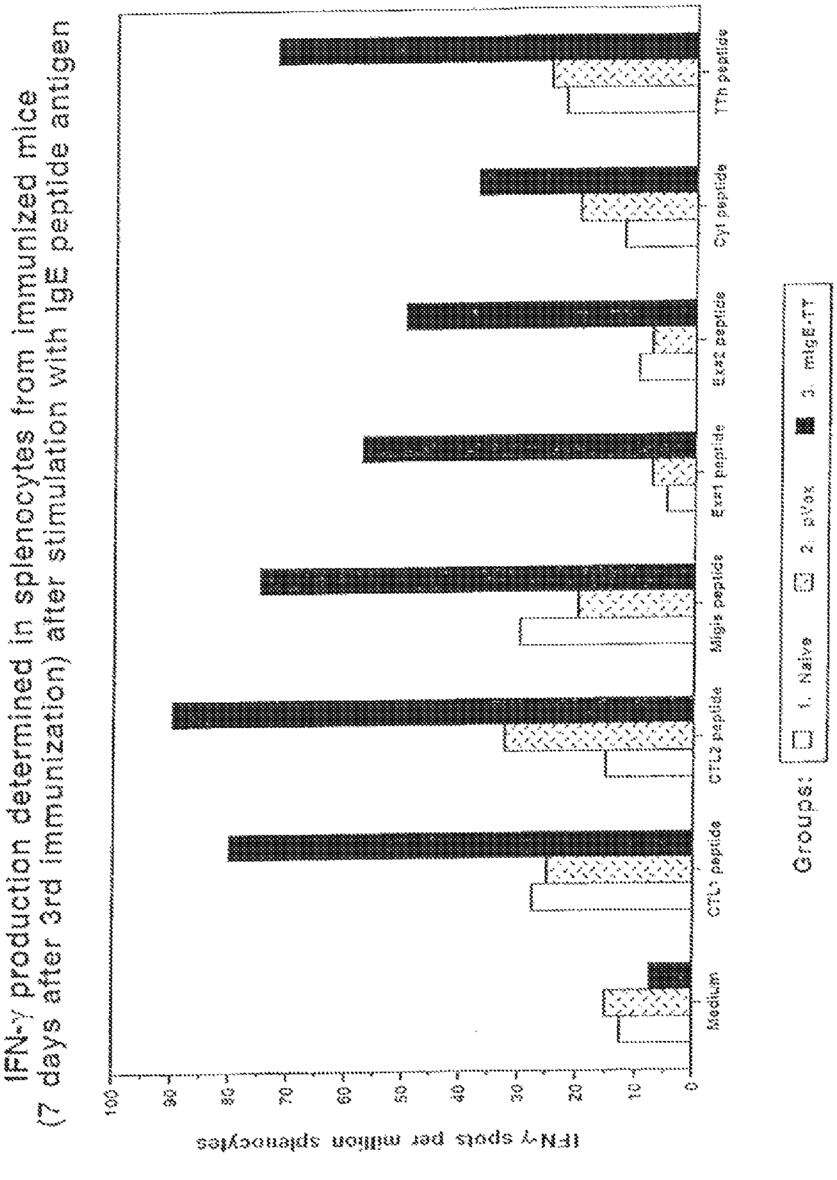
FIG. 8 shows in vitro assay data Splenocytes from naïve, vector-only immunized and mIge-TT construct immunized mice were isolated and stimulated with the synthetic IgE peptide antigens in FIG. 7 and interferon gamma production was assessed.

M-IgE-TT was constructed as described in the FIGS. 5 and 6 and used to immunize HLA-A2 mice. HLA-A2 mice are transgenic mice which express the human MHC haplotype A2 facilitating testing of the concept of immunization against the IgE molecule and targeting the portion of the IgE molecule that is expressed only on producer cells. Theses epitopes are not present in cells that bind IgE. Synthetic peptides shown in FIG. 7 were made to use as antigens in in vitro assays. As shown in FIG. 8 a strong cellular response is induced by M-IgE-TT that targets relevant peptide epitopes expressed by IgE producing cells. The construct was highly effective at inducing these epitope specific responses.

The invention claimed is:

1. A method of treating an individual who has been identified as being susceptible to an IgE mediated allergic disease or condition, the method comprising the step of administering to such an individual a prophylactically effective amount of a vaccine that comprises a nucleic acid molecule that encodes a fusion protein that comprises an epitope of membrane IgE and is free of epitopes of serum IgE, that encodes a non-IgE helper T cell epitope, and that encodes a proteolytic cleavage sequence between said epitope of membrane IgE and said non-IgE helper T cell epitope, wherein the proteolytic cleavage sequence is REKRAVYG (amino acids 140-147 of SEQ ID NO:6).

2. A method of treating an individual who has been identified as having an IgE mediated allergic disease or condition, the method comprising the step of administering to such an individual a therapeutically effective amount of a vaccine that comprises a nucleic acid molecule that comprises a nucleic acid sequence that encodes a fusion protein that comprises an epitope of membrane IgE and is free of epitopes of serum IgE, that encodes a non-IgE helper T cell epitope, and that encodes a proteolytic cleavage sequence between said epitope of membrane IgE and said non-IgE helper T cell epitope, wherein the proteolytic cleavage sequence is REKRAVYG (amino acids 140-147 of SEQ ID NO:6).

3. The method of claim 1 wherein said fusion protein comprises a leader sequence, said epitope of membrane IgE is an epitope of human membrane IgE, and said proteolytic cleavage site between said epitope of human membrane IgE and said non-IgE helper T cell epitope is cleaved when said fusion protein is present in a human.

4. The method of claim 3, wherein the leader sequence is amino acids 1-18 of SEQ ID NO:6.

5. The method of claim 4, wherein said non-IgE helper T cell epitope is a tetanus toxoid Th epitope.

6. The method of claim 5, wherein said fusion proteins comprises human membrane IgE.

7. The method of claim 6, wherein said nucleic acid molecule is a plasmid.

8. The method of claim 1 wherein said protein that comprises said epitope of membrane IgE and is free of epitopes of serum IgE comprises membrane IgE or fragment thereof.

9. The method of claim 1 wherein said protein that comprises said epitope of membrane IgE and is free of epitopes of serum IgE comprises membrane IgE.

10. The method of claim 1 wherein said non-IgE helper T cell epitope is a tetanus toxoid Th epitope.

11. The method of claim 1 wherein the nucleic acid molecule is a plasmid.

12. The method of claim 1 wherein said protein that comprises said epitope of membrane IgE and is free of epitopes of serum IgE further comprises a leader sequence.

13. The method of claim 2 wherein said fusion protein comprises a leader sequence, said epitope of membrane IgE is an epitope of human membrane IgE, and said proteolytic cleavage site between said epitope of human membrane IgE and said non-IgE helper T cell epitope is cleaved when said fusion protein is present in a human.

14. The method of claim 13, wherein the leader sequence is amino acids 1-18 of SEQ ID NO:6.

15. The method of claim 14, wherein said non-IgE helper T cell epitope is a tetanus toxoid Th epitope.

16. The method of claim 15, wherein said fusion proteins comprises human membrane IgE.

17. The method of claim 16, wherein said nucleic acid molecule is a plasmid.

18. The method of claim 2 wherein said protein that comprises said epitope of membrane IgE and is free of epitopes of serum IgE comprises membrane IgE or fragment thereof.

19. The method of claim 2 wherein said protein that comprises said epitope of membrane IgE and is free of epitopes of serum IgE comprises membrane IgE.

20. The method of claim 2 wherein said non-IgE helper T cell epitope is a tetanus toxoid Th epitope.

21. The method of claim 2 wherein the nucleic acid molecule is a plasmid.

22. The method of claim 2 wherein said protein that comprises said epitope of membrane IgE and is free of epitopes of serum IgE further comprises a leader sequence.

* * * * *

SEQUENCE LISTING

```
<160> NUMBER OF SEQ ID NOS: 13

<210> SEQ ID NO 1
<211> LENGTH: 88
<212> TYPE: DNA
<213> ORGANISM: Artificial Sequence
<220> FEATURE:
<223> OTHER INFORMATION: IgE primer 1

<400> SEQUENCE: 1

cccaagctta tggactggac ctggatcctc ttcttggtgg cagcagccac gcgagtccac     60

tcccatgggc tggctggcgg ctccgcgc                                        88


<210> SEQ ID NO 2
<211> LENGTH: 30
<212> TYPE: DNA
<213> ORGANISM: Artificial Sequence
<220> FEATURE:
<223> OTHER INFORMATION: IgE primer 2

<400> SEQUENCE: 2

ccgctcgagc gtggggctgg aggacgttgg                                      30


<210> SEQ ID NO 3
<211> LENGTH: 87
<212> TYPE: DNA
<213> ORGANISM: Artificial Sequence
<220> FEATURE:
<223> OTHER INFORMATION: IgE primer 3

<400> SEQUENCE: 3

ccgctcgaga gaaacgagct gtcgtaggat ccgatccaaa ttatttaagg actgattctg     60

ataaagatag atttttacaa accatgg                                         87


<210> SEQ ID NO 4
<211> LENGTH: 88
<212> TYPE: DNA
<213> ORGANISM: Artificial Sequence
<220> FEATURE:
<223> OTHER INFORMATION: IgE primer 4

<400> SEQUENCE: 4

ccggaattct taattctgtt aaacagtttt accatggttt gtaaaaatct atctttatca     60

gaatcagtcc ttaaataatt tggatcgg                                        88


<210> SEQ ID NO 5
<211> LENGTH: 630
<212> TYPE: DNA
<213> ORGANISM: Artificial Sequence
<220> FEATURE:
<223> OTHER INFORMATION: mIgE-TT construct nucleic acid

<400> SEQUENCE: 5

atggactgga cctggatcct cttcttggtg gcagcagcca cgcgagtcca ctcccatggg     60

ctggctggcg gctccgcgca gtcccagagg gccccggata gggtgctctg ccactccgga    120

cagcagcagg gactgccgag agcagcagga ggctctgtcc cccacccccg ctgccactgt    180
```

-continued

```
ggagccggga gggctgactg gccaggtccc ccagagctgg acgtgtgcgt ggaggaggcc    240

gagggcgagg cgccgtggac gtggaccggc ctctgcatct tcgccgcact cttcctgctc    300

agcgtgagct acagcgccgc cctcacgctc ctcatggtgc agcggttcct ctcagccacg    360

cggcagggga ggccccagac ctccctcgac tacaccaacg tcctccagcc ccacgccaga    420

gaaaaaagag ctgttgttgg ttacgatcca aattatttaa ggactgattc tgataaagat    480

agatttttac aaaccatggt aaaactgttt aacagaatta agagagaaaa aagagctgtt    540

gttggtttta ataattttac cgttagcttt tggttgaggg ttcctaaagt atctgctagt    600

catttagaac atcatcatca tcatcattag                                     630
```

```
<210> SEQ ID NO 6
<211> LENGTH: 209
<212> TYPE: PRT
<213> ORGANISM: Artificial Sequence
<220> FEATURE:
<223> OTHER INFORMATION: mIgE-TT construct amino acid sequence

<400> SEQUENCE: 6

Met Asp Trp Thr Trp Ile Leu Phe Leu Val Ala Ala Ala Thr Arg Val
1               5                   10                  15

His Ser His Gly Leu Ala Gly Gly Ser Ala Gln Ser Gln Arg Ala Pro
            20                  25                  30

Asp Arg Val Leu Cys His Ser Gly Gln Gln Gln Gly Leu Pro Arg Ala
        35                  40                  45

Ala Gly Gly Ser Val Pro His Pro Arg Cys His Cys Gly Ala Gly Arg
    50                  55                  60

Ala Asp Trp Pro Gly Pro Pro Glu Leu Asp Val Cys Val Glu Glu Ala
65                  70                  75                  80

Glu Gly Glu Ala Pro Trp Thr Trp Thr Gly Leu Cys Ile Phe Ala Ala
                85                  90                  95

Leu Phe Leu Leu Ser Val Ser Tyr Ser Ala Ala Leu Thr Leu Leu Met
            100                 105                 110

Val Gln Arg Phe Leu Ser Ala Thr Arg Gln Gly Arg Pro Gln Thr Ser
        115                 120                 125

Leu Asp Tyr Thr Asn Val Leu Gln Pro His Ala Arg Glu Lys Arg Ala
    130                 135                 140

Val Val Gly Tyr Asp Pro Asn Tyr Leu Arg Thr Asp Ser Asp Lys Asp
145                 150                 155                 160

Arg Phe Leu Gln Thr Met Val Lys Leu Phe Asn Arg Ile Lys Arg Glu
                165                 170                 175

Lys Arg Ala Val Val Gly Phe Asn Asn Phe Thr Val Ser Phe Trp Leu
            180                 185                 190

Arg Val Pro Lys Val Ser Ala Ser His Leu Glu His His His His His
        195                 200                 205

His


<210> SEQ ID NO 7
<211> LENGTH: 22
<212> TYPE: PRT
<213> ORGANISM: Artificial Sequence
<220> FEATURE:
<223> OTHER INFORMATION: Antigen 1

<400> SEQUENCE: 7

Ser Ala Gln Ser Gln Arg Ala Pro Asp Arg Val Leu Cys His Ser Gly
1               5                   10                  15
```

-continued

```
Gln Gln Gln Gly Leu Pro
            20


<210> SEQ ID NO 8
<211> LENGTH: 22
<212> TYPE: PRT
<213> ORGANISM: Artificial Sequence
<220> FEATURE:
<223> OTHER INFORMATION: Antigen peptide 2

<400> SEQUENCE: 8

Ala Gly Gly Ser Val Pro His Pro Arg Cys His Cys Gly Ala Gly Arg
1               5                   10                  15

Ala Asp Trp Pro Gly Pro
            20


<210> SEQ ID NO 9
<211> LENGTH: 15
<212> TYPE: PRT
<213> ORGANISM: Artificial Sequence
<220> FEATURE:
<223> OTHER INFORMATION: Antigen peptide 3

<400> SEQUENCE: 9

Glu Leu Asp Val Cys Val Glu Glu Ala Glu Gly Glu Ala Pro Trp
1               5                   10                  15


<210> SEQ ID NO 10
<211> LENGTH: 9
<212> TYPE: PRT
<213> ORGANISM: Artificial Sequence
<220> FEATURE:
<223> OTHER INFORMATION: Antigen peptide 4

<400> SEQUENCE: 10

Glu Ala Pro Trp Thr Trp Thr Gly Leu
1               5


<210> SEQ ID NO 11
<211> LENGTH: 10
<212> TYPE: PRT
<213> ORGANISM: Artificial Sequence
<220> FEATURE:
<223> OTHER INFORMATION: Antigen peptide 5

<400> SEQUENCE: 11

Thr Gly Leu Cys Ile Phe Ala Ala Leu Phe
1               5                   10


<210> SEQ ID NO 12
<211> LENGTH: 27
<212> TYPE: PRT
<213> ORGANISM: Artificial Sequence
<220> FEATURE:
<223> OTHER INFORMATION: Antigen peptide 6

<400> SEQUENCE: 12

Val Gln Arg Phe Leu Ser Ala Thr Arg Gln Gly Arg Pro Gln Thr Ser
1               5                   10                  15

Leu Asp Tyr Thr Asn Val Leu Gln Pro His Ala
            20                  25


<210> SEQ ID NO 13
<211> LENGTH: 27
<212> TYPE: PRT
```

-continued

```
<213> ORGANISM: Artificial Sequence
<220> FEATURE:
<223> OTHER INFORMATION: Antigen peptide 7

<400> SEQUENCE: 13

Tyr Asp Pro Asn Tyr Leu Arg Thr Asp Ser Asp Lys Asp Arg Phe Leu
1               5                   10                  15

Gln Thr Met Val Lys Leu Phe Asn Arg Ile Lys
            20                  25
```